United States Patent [19]

Matthews et al.

[11] Patent Number: 4,505,705
[45] Date of Patent: Mar. 19, 1985

[54] SANITARY NAPKIN WITH FOLLOWING BAFFLE

[75] Inventors: Billie J. Matthews, Winnebago County; S. Richard Bornslaeger, Outagamie County, both of Wis.

[73] Assignee: Kimberly-Clark Corporation, Neenah, Wis.

[21] Appl. No.: 471,599

[22] Filed: Mar. 3, 1983

[51] Int. Cl.³ .............................................. A61F 13/16
[52] U.S. Cl. .................................... 604/385; 604/366; 604/370
[58] Field of Search ............... 604/366, 370, 378, 379, 604/380

[56] References Cited

U.S. PATENT DOCUMENTS 4,333,465 6/1982 Wiegner .............................. 604/380
4,397,644 8/1983 Matthews et al. .................. 604/378

Primary Examiner—C. Fred Rosenbaum
Assistant Examiner—Sherri E. Vinyard
Attorney, Agent, or Firm—Howard Olevsky

[57] ABSTRACT

A sanitary napkin with an absorbent batt which has been folded upon itself along each longitudinal edge and then folded inwardly to provide a three layer absorbent batt. The sanitary napkin has a fluid permeable wrap which overlies each outer and inner fold and terminates at the outer edges of the third layer. A fluid impermeable baffle is positioned between the multiple layers of absorbent and the wrap except on the top, i.e., body facing surface of the absorbent batt.

5 Claims, 2 Drawing Figures

SANITARY NAPKIN WITH FOLLOWING BAFFLE

FIELD OF THE INVENTION

The subject invention relates to a sanitary napkin and particularly a sanitary napkin with a multi layer folded absorbent component.

BACKGROUND OF THE INVENTION

Recently it has been found that sanitary napkins containing absorbent layers having thermoplastic material have certain advantages over such napkins utilizing only conventional cellulosic material as an absorbent. The presence of thermoplastic material adds resiliency to the absorbent and also tends to prevent the collapse of capillaries of cellulosic material when the two materials are blended together. Examples of patents which discuss the utilization of thermoplastic material in conjunction with cellulosic material for sanitary appliances are: U.S. Pat. Nos. 4,082,886 and 4,129,132 issued to George A. M. Butterworth et al; 3,976,074 issued to Harry G. Fitzgerald et al; 4,054,141 issued to Julius Schwaiger et al; 4,047,531 issued to Hamzeh Karami; 3,545,441 issued to Gunnar Gravdahl and 4,219,024 issued to Donald Patience et al.

The above patents also describe the concept of sanitary napkins with multilayer absorbents.

It has been recently determined that sanitary napkins with multilayer absorbents in which the layers are formed by folding provide increased comfort not only in the folded areas, but also with regard to resistance to permanent distortion and resiliency. These features are particularly enhanced when thermoplastic fibers are utilized throughout the folded absorbent batt. When thermoplastic fibers are present, the resistance to permanent compressibility is enhanced because of the presence of each individual fold. Bearing this in mind, a napkin in which an absorbent batt with thermoplastic fibers has been folded repeatedly upon itself should be substantially more comfortable than one without this feature.

Where thermoplastic fibers have been utilized, however, there is generally a decrease in total absorbent capacity, especially when the fibers are present in amounts sufficient to add resiliency.

SUMMARY OF THE INVENTION

According to this invention a sanitary napkin is provided in which an absorbent batt is folded inward along each longitudinal edge and then folded again to provide three separate absorbent layers, a fluid permeable wrap which extends over the top of the absorbent batt forming the first layer and extends over the folded portions of the multiple layers formed from the absorbent batt. The napkin defined by this invention employs a fluid impermeable baffle between the absorbent batt and the wrap in all areas except the portion of the napkin designed to abut the body of the wearer.

DETAILED DESCRIPTION OF THE INVENTION AND DRAWINGS

Figure 1:
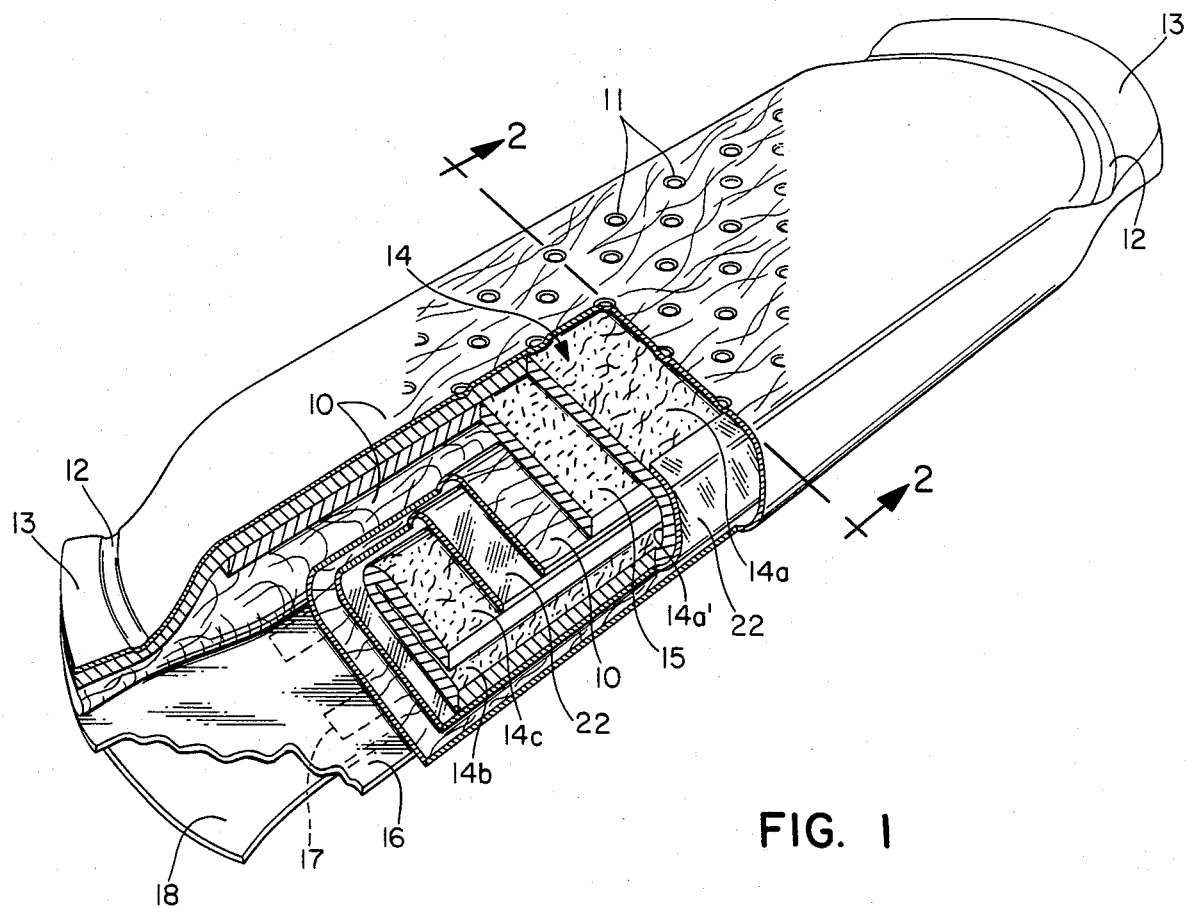
Figure 2:
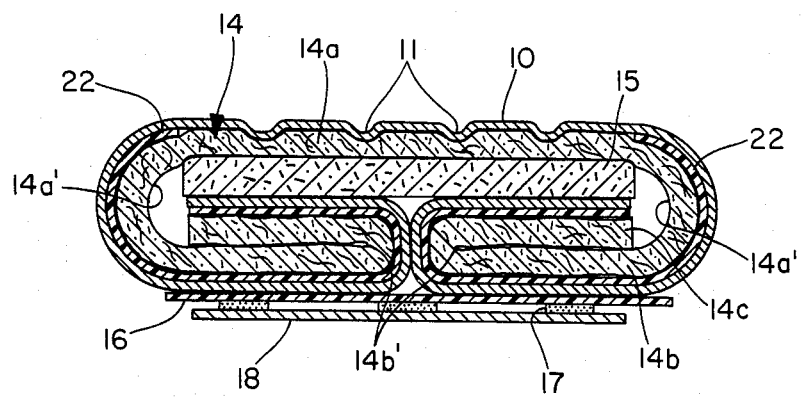

This invention may be more readily understood by reference to the drawings in which FIG. 1 is a perspective view partially in cross-section and FIG. 2 is a side cross sectional view taken along the lines 2—2 of FIG. 1.

As can be seen by reference to the figures, a sanitary napkin is provided with the first absorbent batt 14 having an upper absorbent layer 14a, a second absorbent layer 14b comprised of two identical legs of material formed by the folds 14a made along each longitudinal axis. A third absorbent layer 14c has two separate legs which extend over the legs formed on layer 14b as a result of the folds shown at 14b.

The absorbent batt 14 contains thermoplastic material which adds resiliency with additional resiliency being added as a result of the multiple layers formed by folds 14a and 14b. The percentage of thermoplastic material can vary anywhere from 10 to 100% in this layer.

In the particular embodiment depicted in FIGS. 1 and 2 an intermediate absorbent layer 15 is illustrated. This particular absorbent layer is designed to have increased capacity when compared to absorbent batt 14. Due to the particularly high level of built in resiliency inherent in absorbent batt 14, resiliency need not be taken into account to any large extent for this intermediate layer 15. Layer 15 may be any one of a number of relatively high capacity absorbent material such as conventional wood pulp fluff or superabsorbent. A particularly preferred material is that described in U.S. Pat. No. 4,372,312 which is a surfactant treated meltblown microfibrous web. This particular web is characterized by high fluid wicking ability and may be used alone or in combination with superabsorbent wood pulp fluff or the like.

Referring to FIG. 1, the wrap 10 overlies layer 14a of batt 14 and extends around each fold 14a and further extends over the outer, i.e., bottom portion of each leg making up layer 14b, over each folded section 14b and terminates at the inward extremes of the layer 14c.

The internal baffle 22 is located between the wrap 10 and absorbent layer 14 except at the top surface of the pad at least in an area corresponding to the perineal area of the wearer. The internal or following baffle 22 defines pathways of fluid flow along the sides of batt 14 to minimize leakage from that batt and also serves to provide entrapment pathways for the amount of fluid which is taken up but not retained by layer 15.

The baffle may be of any conventional thermoplastic material as is known in the art and its particular composition is not part of this invention. As is shown in FIGS. 1 and 2, the wrap material 10 can be bound to layers 14 at sites 11 by fusing ultrasonic bonding or the like to enhance fluid conductivity through the absorbent layer 14a.

The embodiment depicted in FIGS. 1 and 2 show a second baffle 16 which is added to increase the structural stability of the napkin in a preferred embodiment of this invention and, as can be seen more clearly from FIG. 2, the baffle 16 has three lines of adhesive 17 attached thereto and a release liner for the adhesive 18. The napkin is sealed in a conventional matter at either end by ultrasonic means shown as a clear area on the thermoplastic wrap material 12 leaving free tab ends 13.

A napkin made according to this invention is manufactured preferably by zone coextruding the thermoplastic baffle on a nonwoven wrap. Such a process is described for example in U.S. Pat. No. 3,356,556 and is not part of the claimed invention.

The baffle may of course be cut in strips and adhesively attached or separately fused as alternative process methods. The batt 14 is then appropriately positioned on the baffle and wrap combination and the two are folded twice along each edge of the combination to form the structure depicted in this invention. If an additional absorbent layer or layers 15 is to be used they are, of course, positioned during the folding step.

What is claimed is:

1. An elongate sanitary napkin with essentially parallel longitudinal fold edges comprising, in combination:
   (a) a first absorbent batt containing thermoplastic fibers with three horizontally disposed layers said batt having:
      (1) a first layer with a continuous surface,
      (2) a second layer with legs extending inward toward the longitudinal center of the pad formed by folding said first layer inward along each longitudinal edge;
      (3) a third layer positioned between said first and second layers having legs overlying the legs of said second layer extending toward each longitudinal edge of said napkin from the longitudinal center and formed by folding each leg of said second layer inwardly upon itself said folding inwardly facing folds positioned proximally to each other near the longitudinal center of the pad;
   (b) a fluid permeable wrap overlying said first layer, the extreme portion of said folds forming the legs of said second layer, and the exterior portion of the folds forming the legs of said third layer and terminating at the ends of said legs of said third layer; and
   (c) a fluid impermeable baffle positioned between said wrap and said absorbent except for that section of said wrap overlying the central portion of said first layer said baffle providing pathways for fluid flow within the napkin.

2. The napkin according to claim 1 wherein said folds forming said third layer are attached to each other.

3. The napkin according to claim 1 or 2 wherein a second absorbent batt is interposed between said first and third layers of said first absorbent batt.

4. The napkin according to claim 1 or 2 wherein a second fluid impervious baffle is attached to the wrap overlying the legs of said second layer and said fold forming said third layer.

5. The sanitary napkin according to claim 1 wherein the cover is spacedly fused to said first layer.

* * * * *